(12) United States Patent
Miura et al.

(10) Patent No.: US 8,586,786 B2
(45) Date of Patent: Nov. 19, 2013

(54) METHOD FOR PRODUCING CATALYST FOR USE IN PRODUCTION OF UNSATURATED ALDEHYDE AND/OR UNSATURATED CARBOXYLIC ACID, AND METHOD FOR PRODUCING UNSATURATED ALDEHYDE AND/OR UNSATURATED CARBOXYLIC ACID

(75) Inventors: Naoki Miura, Niihama (JP); Eiichi Shiraishi, Niihama (JP); Koichi Nagai, Saijo (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/555,840

(22) Filed: Jul. 23, 2012

(65) Prior Publication Data

US 2012/0289741 A1 Nov. 15, 2012

Related U.S. Application Data

(62) Division of application No. 12/467,079, filed on May 15, 2009, now Pat. No. 8,252,714.

(30) Foreign Application Priority Data

May 16, 2008 (JP) .................. 2008-129200

(51) Int. Cl.
*C07C 229/00* (2006.01)
*C07C 45/00* (2006.01)
*B01J 23/00* (2006.01)
*B01J 23/32* (2006.01)

(52) U.S. Cl.
USPC ........... 562/546; 568/479; 502/306; 502/307; 502/308; 502/309; 502/310; 502/311; 502/313; 502/314; 502/315; 502/316; 502/317; 502/321; 502/322; 502/323; 502/324

(58) Field of Classification Search
USPC .................. 562/546; 568/479; 502/306–311, 502/313–317, 321–324
See application file for complete search history.

(56) References Cited

U.S. PATENT DOCUMENTS

| | | | |
|---|---|---|---|
| 3,746,656 A | 7/1973 | Shiraishi et al. | |
| 4,547,484 A | 10/1985 | Li | |
| 4,816,603 A | 3/1989 | Oh-Kita et al. | |
| 4,916,103 A | 4/1990 | Martan et al. | |
| 5,166,119 A | 11/1992 | Oh-Kita et al. | |
| 6,479,691 B1 | 11/2002 | Sasaki et al. | |
| 6,545,177 B2 | 4/2003 | Tanimoto et al. | |
| 6,559,085 B1 | 5/2003 | Sasaki et al. | |
| 6,583,316 B1 | 6/2003 | Onodera et al. | |
| 6,629,973 B1 | 10/2003 | Wårdell et al. | |
| 6,784,134 B2 | 8/2004 | Kasuga et al. | |
| 6,878,847 B2 | 4/2005 | Kasuga et al. | |
| 6,916,763 B2 | 7/2005 | Tway | |
| 6,982,343 B2 | 1/2006 | Chaturvedi et al. | |
| 7,012,039 B2 | 3/2006 | Watanabe et al. | |
| 7,129,195 B2 | 10/2006 | Felder et al. | |
| 7,161,044 B2 * | 1/2007 | Nakamura et al. | 568/476 |
| 7,208,445 B2 | 4/2007 | Bogan et al. | |
| 7,208,636 B2 * | 4/2007 | Petzoldt et al. | 568/476 |
| 7,262,148 B2 | 8/2007 | Teshigahara et al. | |
| 7,265,250 B2 * | 9/2007 | Shin et al. | 568/479 |
| 7,279,442 B2 | 10/2007 | Teshigahara et al. | |
| 7,326,668 B2 | 2/2008 | Bogan et al. | |
| 7,341,974 B2 | 3/2008 | Kang et al. | |
| 7,361,791 B2 * | 4/2008 | Liang et al. | 568/476 |
| 7,365,041 B2 | 4/2008 | Miyaki et al. | |
| 7,388,107 B2 * | 6/2008 | Jinno et al. | 562/545 |
| 7,396,955 B2 | 7/2008 | Gaffney et al. | |
| 7,524,792 B2 | 4/2009 | Dieterle et al. | |
| 7,544,633 B2 | 6/2009 | Kang et al. | |
| 7,579,297 B2 * | 8/2009 | Kondo et al. | 502/311 |
| 7,632,777 B2 | 12/2009 | Teshigahara et al. | |
| 7,731,919 B2 * | 6/2010 | Fukumoto | 422/236 |
| 7,807,600 B2 | 10/2010 | Watanabe et al. | |
| 7,888,281 B2 | 2/2011 | Lin et al. | |
| 7,906,689 B2 | 3/2011 | Zhuang et al. | |
| 2002/0198103 A1 | 12/2002 | Kasuga et al. | |

FOREIGN PATENT DOCUMENTS

| | | |
|---|---|---|
| EP | 0 574 895 A1 | 12/1993 |
| JP | 5-97730 A | 4/1993 |
| JP | 5-293359 A | 11/1993 |
| JP | 6-381 A | 1/1994 |
| JP | 9-52053 A | 2/1997 |
| JP | 2002-273229 A | 9/2002 |
| JP | 2004-2208 A | 1/2004 |
| JP | 2007-117866 A | 5/2007 |

OTHER PUBLICATIONS

Search and Examination Report issued on May 12, 2010 in corresponding Singapore Patent Application No. 200903050-3.
Japanese Office Action in Japanese counterpart Application No. 2008-129200, dated Aug. 28, 2012, with English language translation.

* cited by examiner

*Primary Examiner* — Cam N. Nguyen
(74) *Attorney, Agent, or Firm* — Birch, Stewart, Kolasch & Birch, LLP

(57) ABSTRACT

A catalyst for use in the production of an unsaturated aldehyde and/or an unsaturated carboxylic acid, the catalyst comparing (or, preferably, being composed of) a mixed oxide containing molybdenum, bismuth and iron, which has improved methanical strength, is produced by a method including the steps of (1) drying an aqueous solution or an aqueous slurry containing raw materials of the catalyst and then firstly calcining a dried product in a molecular oxygen-containing gas atmosphere to obtain a calcined product; (2) heating the calcined product obtained in Step (1) in the presence of a reducing material to obtain a reduced product having a mass loss of 0.05 to 6%; and (3) secondly calcining the reduced product obtained in Step (2) in a molecular oxygen-containing gas atmosphere.

1 Claim, No Drawings

METHOD FOR PRODUCING CATALYST FOR USE IN PRODUCTION OF UNSATURATED ALDEHYDE AND/OR UNSATURATED CARBOXYLIC ACID, AND METHOD FOR PRODUCING UNSATURATED ALDEHYDE AND/OR UNSATURATED CARBOXYLIC ACID

This application is a divisional of application Ser. No. 12/467,079, filed on May 15, 2009 and issued as U.S. Pat. No. 8,252,714, which claims priority under 35 U.S.C. §119(a) to Patent Application No. 2008-129200 filed in Japan on May 16, 2008, all of which are hereby expressly incorporated by reference into the present application and for which priority is claimed under 35 U.S.C. §120.

FIELD OF THE INVENTION

The present invention relates to a method for producing a catalyst for use in the production of an unsaturated aldehyde and/or an unsaturated carboxylic acid. The present invention also relates to a method for producing an unsaturated aldehyde and/or an unsaturated carboxylic acid by using a catalyst prepared by the foregoing method.

DESCRIPTION OF PRIOR ART

A catalyst composed of a mixed oxide comprising molybdenum, bismuth and iron is effective as a catalyst to be used for producing acrolein and/or acrylic acid by a gas phase catalytic oxidation of propylene with molecular oxygen, and also effective as a catalyst to be used for producing methacrolein and/or methacrylic acid by a gas phase catalytic oxidation of isobutylene or tert-butyl alcohol with molecular oxygen. It is known that such a catalyst is prepared generally by drying an aqueous solution or an aqueous slurry containing catalyst components and then calcining the dried product. In the use of this type of catalyst for the above oxidation reactions, the catalyst is filled in the form of a molded catalyst or a supported catalyst in a fixed bed reactor. If the catalyst has low mechanical strength, it tends to be broken when it is filled in a reactor and, as a result, a pressure drop occurs in the reactor during the reaction. Therefore, such a catalyst is required to have high mechanical strength.

To increase the mechanical strength of a catalyst, the compounding of inorganic fiber in a catalyst during the preparation thereof is proposed (see JP-A-06-000381, JP-A-2002-273229 and JP-A-09-052053).

However, a catalyst prepared by the above method may not necessarily have satisfactory mechanical strength.

SUMMARY OF THE INVENTION

An object of the present invention is to provide a method for producing a catalyst for use in the production of an unsaturated aldehyde and/or an unsaturated carboxylic acid, which catalyst comprises a mixed oxide comprising molybdenum, bismuth and iron and has improved mechanical strength.

As the result of extensive studies by the present inventors, it has been found that the above object can be accomplished when a catalyst for use in the production of an unsaturated aldehyde and/or an unsaturated carboxylic acid, the catalyst comprising (or, preferably, being composed of) a mixed oxide containing molybdenum, bismuth and iron, is used which is produced by a method comprising Step (1), (2) and (3) described below.

Thus, the present invention provides a method for producing a catalyst for use in the production of an unsaturated aldehyde and/or an unsaturated carboxylic acid, the catalyst comprising (or, preferably, being composed of) a mixed oxide comprising molybdenum, bismuth and iron, said method comprising the steps of (1) drying an aqueous solution or an aqueous slurry containing raw materials of the catalyst and then firstly calcining a dried product in a molecular oxygen-containing gas atmosphere to obtain a calcined product;

(2) heating the calcined product obtained in Step (1) in the presence of a reducing material to obtain a reduced product having a mass loss, represented by the following equation (I), of 0.05 to 6%;

$$\text{Mass loss}(\%) = [(Wa - Wb)/Wa] \times 100 \quad (I)$$

in which Wa is a weight of a calcined product before the reduction treatment, and Wb is a weight of a reduced product after the reduction treatment; and (3) secondly calcining the reduced product obtained in Step (2) in a molecular oxygen-containing gas atmosphere.

Furthermore, the present invention provides a method for producing an unsaturated aldehyde and/or an unsaturated carboxylic acid comprising the steps of:

producing a catalyst by the method for the production of the catalyst according to the present invention, and a gas phase catalytic oxidation of at least one compound selected from the group consisting of propylene, isobutylene and tert-butyl alcohol with molecular oxygen in the presence of the catalyst produced in the above step.

The method of the present invention can provide a catalyst having better mechanical strength for use in the production of an unsaturated aldehyde and/or an unsaturated carboxylic acid. Moreover, when the catalyst produced by the method of the present invention is used in the production of an unsaturated aldehyde and/or an unsaturated carboxylic acid, the breakage of the catalyst is well prevented during filling it in a reactor. As a result, it is possible to reduce the pressure drop during the reaction and to catalytically oxidize a compound selected from the group consisting of propylene, isobutylene and tert-butyl alcohol stably with molecular oxygen in a vapor phase to produce an unsaturated aldehyde and/or an unsaturated carboxylic acid.

DETAILED DESCRIPTION ON THE INVENTION

The catalyst for use in the production of an unsaturated aldehyde and/or an unsaturated carboxylic acid according to the present invention comprises (or, preferably, is composed of) a mixed oxide comprising molybdenum, bismuth and iron as the essential elements. The mixed oxide may optionally contain at least one element other than molybdenum, bismuth and iron. For example, the mixed oxide may preferably contain at lease one element selected from the group consisting of nickel, cobalt, potassium, rubidium, cesium and thallium.

A preferable example of such a mixed oxide is a compound represented by the following formula (II):

$$Mo_aBi_bFe_cA_dB_eC_fD_gO_x \quad (II)$$

wherein

Mo, Bi and Fe represent molybdenum, bismuth and iron, respectively,

A represents nickel and/or cobalt,

B represents an element selected from the group consisting of manganese, zinc, calcium, magnesium, tin and lead, C represents an element selected from the group consisting of phosphorus, boron, arsenic, tellurium, tungsten, antimony, silicon, aluminum, titanium, zirconium and cerium,

D represents an element selected from the group consisting of potassium, rubidium, cesium and thallium, O represents oxygen, a, b, c, d, e, f and g satisfy the following relationships: $0 \leq b \leq 10$, $0 \leq c \leq 10$, $1 \leq d \leq 10$, $0 \leq e \leq 10$, $0 \leq f \leq 10$ and $0 \leq g \leq 2$, when a is set equal to 12, and x is a value determined depending upon the oxidation states of the other elements. For example, x may be determined by multiplying the valence of each element (except for oxygen) comprised in the mixed oxide with its corresponding stoichiometric proportion within the mixed oxide, and adding up the multiplication products to form a sum, whereby the sum thus formed divided by 2 equals x. Accordingly, if the mixed oxide is, for example, $Mo_{12}Bi_5Fe_4Co_{10}CsO_x$ and the valences of Mo, Bi, Fe, Co and Cs in this compound are VI, III, III, II and I, respectively, x can be determined by the above method as $x=[(12\cdot6)+(3\cdot5)+(3\cdot4)+(2\cdot10)+(1\cdot1)]/2=60$ (i.e., the mixed oxide would have the formula $Mo_{12}Bi_5Fe_4Co_{10}CsO_{60}$).

Among the compounds represented by formula (II), those having the following compositions (except for oxygen atoms) are preferably used:

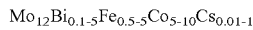
$Mo_{12}Bi_{0.1-5}Fe_{0.5-5}Co_{5-10}Cs_{0.01-1}$

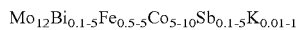
$Mo_{12}Bi_{0.1-5}Fe_{0.5-5}Co_{5-10}Sb_{0.1-5}K_{0.01-1}$

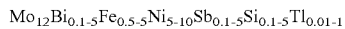
$Mo_{12}Bi_{0.1-5}Fe_{0.5-5}Ni_{5-10}Sb_{0.1-5}Si_{0.1-5}Tl_{0.01-1}$

Hereinafter, a method for producing the catalyst according to the present invention is explained. An aqueous solution or an aqueous slurry containing raw materials of the catalyst is dried and then, the dried product is calcined firstly in a molecular oxygen-containing gas atmosphere [Step (1)]. As the raw materials of the catalyst, in general, compounds of the respective elements constituting the catalyst, such as oxides, nitrates, sulfates, carbonates, hydroxides, oxoacids and ammonium salts thereof, and halides, are used in ratios such that desired atomic ratios of the elements are satisfied. For example, molybdenum trioxide, molybdic acid, ammonium paramolybdate and the like may be used as a molybdenum compound. Bismuth oxide, bismuth nitrate, bismuth sulfate and the like may be used as a bismuth compound. Iron (III) nitrate, iron (III) sulfate, iron (III) chloride and the like may be used as an iron compound. Cobalt nitrate, cobalt sulfate, cobalt chloride and the like may be used as a cobalt compound. Antimony trioxide, antimony (III) chloride and the like may be used as an antimony compound. Cesium nitrate, cesium carbonate, cesium hydroxide and the like may be used as a cesium compound.

The aqueous solution or the aqueous slurry containing the raw materials may be prepared by mixing the raw materials with water. A mixing temperature and an amount of water used may adequately be selected. The aqueous solution or the aqueous slurry may be dried using a kneader, a box dryer, a drum-type through-air dryer, a spray dryer, a flush dryer, or the like.

The dried product obtained by the above drying step is firstly calcined (first calcination) in the molecular oxygen-containing gas atmosphere. The concentration of molecular oxygen in the molecular oxygen-containing gas is usually from 1 to 30% by volume, and preferably from 10 to 25% by volume. Ambient air or pure oxygen is usually used as the source of molecular oxygen. Such a source is used as a molecular oxygen-containing gas, if necessary, after being diluted with nitrogen, carbon dioxide, water, helium, argon, or the like. A calcination temperature in the first calcination step is usually from 300 to 600° C., and preferably from 400 to 550° C. A calcination time in the first calcination step is usually from 5 minutes to 40 hours, and preferably from 1 to 20 hours.

The calcined product resulting from the first calcination is subjected to heat treatment in the presence of a reducing material [Step (2)] to obtain a reduced product having a mass loss of from 0.05 to 6% by weight. Such a treatment conducted in the presence of a reducing material will hereinafter be referred simply as a "reduction treatment". The mass loss is defined by the following equation (I):

$$\text{Mass loss}(\%) = [(Wa - Wb)/Wa] \times 100 \qquad (I)$$

in which Wa is a weight of a calcined product before the reduction treatment, and Wb is a weight of a reduced product after the reduction treatment.

Examples of the reducing material include hydrogen, ammonia, carbon monoxide, hydrocarbons, alcohols, aldehydes and amines. Optionally, two or more of such reducing materials may be used. Preferably, hydrocarbons, alcohols, aldehydes and amines each have 1 to about 6 carbon atoms. Examples of such hydrocarbons include saturated aliphatic hydrocarbons such as methane, ethane, propane, n-butane and isobutane, unsaturated aliphatic hydrocarbons such as ethylene, propylene, α-butylene, β-butylene and isobutylene, and aromatic hydrocarbons such as benzene. Examples of such alcohols include saturated aliphatic alcohols such as methanol, ethanol, n-propyl alcohol, isopropyl alcohol, n-butyl alcohol, isobutyl alcohol, sec-butyl alcohol and tert-butyl alcohol, unsaturated aliphatic alcohols such as allyl alcohol, crotyl alcohol and methallyl alcohol, and aromatic alcohols such as phenol. Examples of such aldehydes include saturated aliphatic aldehydes such as formaldehyde, acetaldehyde, propionaldehyde, n-butylaldehyde and isobutylaldehyde, and unsaturated aliphatic aldehydes such as acrolein, crotonaldehyde and methacrolein. Examples of such amines include saturated aliphatic amines such as methylamine, dimethylamine, trimethylamine, ethylamine, diethylamine and triethylamine, and unsaturated aliphatic amines such as allylamine and diallylamine, and aromatic amines such as aniline.

The reduction treatment is usually conducted by subjecting the calcined product to heat treatment in an atmosphere of a gas containing the reducing material. The concentration of the reducing material in the gas is usually from 0.1 to 50% by volume, and preferably from 3 to 30% by volume. The reducing material may be diluted with nitrogen, carbon dioxide, water, helium, argon, or the like so that such a concentration could be achieved. Molecular oxygen may be present in the reducing atmosphere unless the effect of the reduction treatment is affected. Preferably, no molecular oxygen is present in the reducing atmosphere.

A temperature for the reduction treatment is usually from 200 to 600° C., and preferably from 300 to 500° C. The time of the reduction treatment is usually from 5 minutes to 20 hours and preferably from 30 minutes to 10 hours. It is preferable to conduct the reduction treatment by placing the calcined product in a tubular or box-shaped container and keeping the container ventilated with a gas containing the reducing material. At this time, a gas discharged from the container may be circulated and reused, if necessary.

Accordingly, the reduced product having a mass loss, represented by the above equation (I), of 0.05 to 6% by weight is obtained. The mass loss may be attributed to the loss of lattice oxygen atoms from the calcined product, which results in the formation of the reduced product. Therefore, the mass loss of the calcined product may be used as an indicator to monitor the progress of reduction. When the progress of reduction is small, sufficient effects of the reduction may not be attained. When the calcined product is excessively reduced, heat is abruptly generated in the second calcination step carried out in a molecular oxygen-containing atmosphere, which will be explained below, so that the temperature control may become difficult. Therefore, the mass loss of the calcined product after the reduction treatment is preferably from 0.1 to 5% by weight.

In the reduction treatment, the reducing material itself, decomposition products derived from the reducing material or the like may remain in the catalyst after the reduction treatment according to the type of the reducing material used, heat treatment conditions or the like. In such a case, the mass loss can be calculated by measuring the weight of the residual material in the catalyst and then calculating the weight after the reduction treatment by subtracting the mass of the residual material from the weight of the catalyst including the residual material. A typical residual material is carbon and, therefore, the mass of the residual material can be determined, for example, by total carbon (TC) analysis.

The reduced product resulting from the reduction treatment is secondly calcined (second calcination) in a molecular oxygen-containing gas atmosphere [Step (3)]. The molecular oxygen concentration of the gas is usually from 1 to 30% by volume, and preferably from 10 to 25% by volume. Ambient air or pure oxygen is usually used as the source of molecular oxygen. Such a source is used as a molecular oxygen-containing gas, if necessary, after being diluted with nitrogen, carbon dioxide, water, helium, argon, or the like. The calcination temperature in the second calcination step is usually from 200 to 600° C., and preferably from 350 to 550° C. The calcination time in the second calcination step is usually from 5 minutes to 20 hours, and preferably from 30 minutes to 10 hours.

The catalyst produced by the method of the present invention is usually molded in a desired form before use. The catalyst may be molded in the form of a ring, a pellet, a sphere or the like by tabletting, extrusion molding or the like. The catalyst components may be supported on a carrier, for example, silica, alumina, silicon carbide and silicon nitride. In the molding, for improving the mechanical strength of the catalyst, inorganic fiber or the like, which is substantially inert to the intended oxidation reaction, may be added as disclosed in, for example, JP-A-09-052053.

The present invention can increase the mechanical strength of the catalyst by performing the second calcination. Therefore, the catalyst is preferably molded before the second calcination. Specifically, it is preferable to mold the dried product obtained by drying the aqueous solution or the aqueous slurry containing the raw materials of the catalyst, the calcined product obtained by the first calcination, or the reduced product obtained by the reducing treatment.

Thus, the method of the present invention can improve the mechanical strength of a catalyst for use in the production of an unsaturated aldehyde and/or an unsaturated carboxylic acid which catalyst comprises (or, preferably, is composed of) a mixed oxide comprising molybdenum, bismuth and iron. Accordingly, the breakage of the catalyst is prevented when it is filled in a reactor. As a result, it is possible to reduce the pressure drop during the reaction, to catalytically oxidize propylene stably with molecular oxygen in a vapor phase to stably produce acrolein and acrylic acid, and to catalytically oxidize isobutylene or tert-butyl alcohol stably with molecular oxygen in a vapor phase to stably produce methacrolein and methacrylic acid.

The vapor-phase catalytic oxidation reaction is usually carried out by filling the catalyst of the present invention in a fixed bed multitubular reactor and feeding a raw material gas containing a raw material compound selected from the group consisting of propylene, isobutylene and tert-butyl alcohol, and molecular oxygen. An air is usually used as a source of molecular oxygen. Besides the raw material compounds and molecular oxygen, the raw material gas may optionally contain nitrogen, carbon dioxide, carbon monoxide, water vapor and the like.

The reaction temperature is usually from 250 to 400° C. The reaction pressure may be reduced pressure, but it is usually from 100 to 500 kPa. The amount of molecular oxygen is usually from 1 to 3 moles per mole of the raw material compound. The space velocity (SV) of the raw material gas is usually from 500 to 5000/h at STP (standard temperature and pressure, such as a temperature of 0° C. and a pressure of 100 kPa).

Examples of the present invention are shown below, but they do not limit the present invention in any way. In the examples, the unit "ml/min" indicating the flow rate of gas is at STP, unless otherwise stated.

Falling Strength Test of Catalyst

A stainless steel mesh having 4.76 mm openings is fixed at the bottom of a metal tube having an inner diameter of 30 mm and a length of 5 m and being arranged almost perpendicularly to the horizontal direction so that the plane of the mesh is substantially horizontal. Then, X g of a catalyst is charged from the top of the metal tube to fall. The fallen catalyst particles are collected and placed on a sieve having 4.76 mm openings, followed by vibration of the sieve. Then, Y g of the catalyst particles remain on the sieve. The falling strength (%) of the catalyst is defined as follows:

$$\text{Falling strength}(\%) = Y/X \times 100(\%)$$

In the Examples, a conversion (%) and a yield are defined as follows:

$$\text{Conversion}(\%) = 100 \times [(\text{moles of supplied isobutylene}) - (\text{moles of unreacted isobutylene})]/(\text{moles of supplied isobutylene})$$

$$\text{Total yield}(\%) = 100 \times (\text{total moles of methacrolein and methacrylic acid})/(\text{moles of supplied isobutylene})$$

EXAMPLE 1

(a) Preparation of Calcined Product [Step (1)]

13,241 g of ammonium molybdate [$(NH_4)_6Mo_7O_{24} \cdot 4H_2O$] was dissolved in 15,000 g of warm water to form Liquid A. Separately, 6,060 g of iron (III) nitrate [$Fe(NO_3)_3 \cdot 9H_2O$], 13,096 g of cobalt nitrate [$Co(NO_3)_2 \cdot 6H_2O$] and 585 g of cesium nitrate [$CsNO_3$] were dissolved in 6,000 g of warm water and subsequently 2,910 g of bismuth nitrate [$Bi(NO_3)_3 \cdot 5H_2O$] was further dissolved to form Liquid B. Liquid B was added to Liquid A while stirring to form a slurry. The slurry was then dried with a flash dryer to obtain a dried product. Nine (9) parts by weight of silica alumina fiber (RFC400-SL produced by Saint-Gobain™) and 2.5 parts by weight of antimony trioxide ($Sb_2O_3$) were added to 100 parts by weight of the dried material. The resulting mixture was molded into a ring form having an outer diameter of 6.3 mm, an inner diameter of 2.5 mm and a length of 6 mm, and then was calcined at 545° C. for 6 hours in an air flow to obtain a calcined product. This calcined product contained 0.96 bismuth atom, 2.4 iron atoms, 7.2 cobalt atoms, 0.48 cesium atom and 0.48 antimony atom per 12 molybdenum atoms.

(b) Reduction Treatment [Step (2)]

Seventy-five (75) ml of the calcined product obtained in the above step (a) was filled in a glass tube, and then a mixed gas of hydrogen/nitrogen (5/95 by volume) was flowed at a flow rate of 300 ml/min. through the glass tube to conduct a reduction treatment at 345° C. for 8 hours. Then, the supply of hydrogen was stopped, and the product was cooled to room temperature while flowing the nitrogen gas alone to obtain a reduced product. The mass loss due to the reduction treatment was 1.04% by weight.

(c) Second Calcination [Step (3)]

The reduced product obtained in the above step (b) was calcined at 350° C. for 3 hours in an air flow to obtain Catalyst A.

(d) Falling Strength Test of Catalyst A

Thirty (30) g of Catalyst A obtained in the above step (c) was subjected to the falling strength test described above. The falling strength of Catalyst A was 91.8%. The result is shown in Table 1.

(e) Oxidation of Isobutylene

Into a glass reaction tube having an inner diameter of 18 mm, 14.3 ml of Catalyst A obtained in the above step (c) was filled after being diluted with 30 g of silicon carbide (SHINANO-RUNDUM GC F16 produced by Shinano Electric Refining Co., Ltd.). An oxidation reaction was conducted at a reaction temperature of 360° C. by supplying a mixed gas of isobutylene/oxygen/nitrogen/steam (1.0/2.0/10.0/2.7 by mole) into the reaction tube at a flow rate of 157.5 ml/min. The conversion of isobutylene and the total yield of methacrolein and methacrylic acid were 98.9% and 79.6%, respectively.

EXAMPLE 2

(a) Preparation of Catalyst [Steps (1), (2) and (3)]

Catalyst B was prepared in the same manner as in the steps (a), (b) and (c) of Example 1 except that the calcining temperature in the step (c) of Example 1 was changed from 350° C. to 370° C.

(b) Falling Strength Test of Catalyst B

Thirty (30) g of Catalyst B obtained in the previous step (a) of this Example was subjected to the falling strength test described above. The falling strength of Catalyst B was 91.9%. The result is shown in Table 1.

EXAMPLE 3

(a) Preparation of Calcined Product [Step (1)]

A calcined product was prepared in the same manner as in Step (a) of Example 1 except that the amount of the silica alumina fiber was changed from 9 parts by weight to 12 parts by weight.

(b) Reducing Treatment [Step (2)]

A reduced product was prepared in the same manner as in Step (b) of Example 1 except that the calcined product obtained in the previous step (a) of this Example was used in place of the calcined product obtained in the step (a) of Example 1. The mass loss due the reduction treatment was 1.06% by weight.

(c) Second Calcination [Step (3)]

The second calcination was carried out in the same manner as in the step (c) of Example 1 except that the reduced product obtained in the previous step (b) of this Example was used in place of the reduced product obtained in the step (b) of Example 1, the calcining temperature was changed from 350° C. to 330° C., and the calcining time was changed from 3 hours to 5 hours. Thereby, Catalyst C was obtained.

(d) Falling Strength Test of Catalyst C

Thirty (30) g of Catalyst C obtained in the previous step (c) of this Example was subjected to the falling strength test described above. The falling strength of Catalyst C was 92.0%. The result is shown in Table 1.

EXAMPLE 4

(a) Preparation of Catalyst [Steps (1), (2) and (3)]

Catalyst D was prepared in the same manner as in the steps (a), (b) and (c) of Example 3 except that the calcining temperature in the step (c) of Example 3 was changed from 330° C. to 420° C.

(b) Falling Strength Test of Catalyst D

Thirty (30) g of Catalyst D obtained in the previous step (a) of this Example was subjected to the falling strength test described above. The falling strength of Catalyst D was 93.3%. The result is shown in Table 1.

COMPARATIVE EXAMPLE 1

(a) Preparation of Catalyst [Step (1) Only]

The procedures of the step (a) of Example 1 were repeated to obtain a calcined product, which was used as Catalyst E.

(b) Falling Strength Test of Catalyst E

Thirty (30) g of Catalyst E obtained in the previous step (a) of this Comparative Example was subjected to the falling strength test described above. The falling strength of Catalyst E was 86.1%. The result is shown in Table 1.

(c) Oxidation of Isobutylene

Isobutylene was oxidized in the same manner as in the step (e) of Example 1 except that Catalyst E obtained in the above step (a) of this Comparative Example was used in place of Catalyst A. The conversion of isobutylene and the total yield of methacrolein and methacrylic acid were 95.1% and 79.4%, respectively.

COMPARATIVE EXAMPLE 2

(a) Preparation of Catalyst [Steps (1) and (2) Only]

The procedures of the steps (a) and (b) of Example 1 were repeated to obtain a reduced product, which is referred to as Catalyst F.

(b) Falling Strength Test of Catalyst F

Thirty (30) g of Catalyst E obtained in the previous step (a) of this Comparative Example was subjected to the falling strength test described above. The falling strength of Catalyst F was 83.8%. The result is shown in Table 1.

COMPARATIVE EXAMPLE 3

(a) Preparation of Catalyst [Step (1) only]

The procedures of the step (a) of Example 3 were repeated to obtain a calcined product, which was used as Catalyst G.

(b) Falling Strength Test of Catalyst G

Thirty (30) g of Catalyst G obtained in the previous step (a) of this Comparative Example was subjected to the falling strength test described above. The falling strength of Catalyst G was 86.4%. The result is shown in Table 1.

COMPARATIVE EXAMPLE 4

(a) Preparation of Catalyst [Steps (1) and (2) Only]

The procedures of the steps (a) and (b) of Example 3 were repeated to obtain a reduced product, which was used as Catalyst H.

(b) Falling Strength Test of Catalyst H

Thirty (30) g of Catalyst H obtained in the previous step (a) of this Comparative Example was subjected to the falling strength test described above. The falling strength of Catalyst H was 84.6%. The result is shown in Table 1.

TABLE 1

| | Catalyst | Mass loss caused by reduction treatment (wt. %) | Second calcination Temp. (° C.) | Second calcination Time (hrs) | Falling strength (%) |
|---|---|---|---|---|---|
| Example 1 | A | 1.04 | 350 | 3 | 91.8 |
| Example 2 | B | 1.04 | 370 | 3 | 91.9 |
| Example 3 | C | 1.06 | 330 | 5 | 92.0 |
| Example 4 | D | 1.06 | 420 | 5 | 93.3 |
| Comp. Ex. 1 | E | — | — | — | 86.1 |
| Comp. Ex. 2 | F | 1.04 | — | — | 83.8 |
| Comp. Ex. 3 | G | — | — | — | 86.4 |
| Comp. Ex. 4 | H | 1.06 | — | — | 84.6 |

What is claimed is:

1. A method for producing an unsaturated aldehyde and/or an unsaturated carboxylic acid, comprising the steps of:
   (1) drying an aqueous solution or an aqueous slurry containing raw materials of a catalyst and then calcining a dried product in a molecular oxygen-containing gas atmosphere to obtain a calcined product;
   (2) heating the calcined product obtained in Step (1) in the presence of a reducing material to obtain a reduced product having a mass loss, represented by the following equation (I), of 0.05 to 6%:

$$\text{Mass loss (\%)} = [(W_a - W_b)/W_a] \times 100 \quad (I)$$

in which $W_a$ is a weight of a calcined product before the reduction treatment, and $W_b$ is a weight of a reduced product after the reduction treatment; and
   (3) calcining the reduced product obtained in Step (2) in a molecular oxygen-containing gas atmosphere to obtain a catalyst comprising a mixed oxide comprising molybdenum, bismuth and iron, and
   (4) performing a gas phase catalytic oxidation of at least one compound selected from the group consisting of propylene, isobutylene and tertbutyl alcohol with molecular oxygen in the presence of the catalyst produced in step (3).

* * * * *